United States Patent [19]

Kuhns et al.

[11] Patent Number: 5,056,356
[45] Date of Patent: Oct. 15, 1991

[54] NONDESTRUCTIVE TESTING OF PENETRABLE MATERIAL BOND INTERFACES

[75] Inventors: David R. Kuhns, Carlsbad; Gerald L. O'Barr, San Diego, both of Calif.

[73] Assignee: General Dynamics Corporation, Space Systems Division, San Diego, Calif.

[21] Appl. No.: 502,713

[22] Filed: Apr. 2, 1990

[51] Int. Cl.$^5$ .................................... G01M 3/32
[52] U.S. Cl. ..................... 73/49.2; 73/37; 73/40
[58] Field of Search ............... 73/37, 49.2 R, 40

[56] References Cited

U.S. PATENT DOCUMENTS

| | | | |
|---|---|---|---|
| 2,403,897 | 7/1946 | Aller | 73/37 |
| 3,893,332 | 7/1975 | Dolan et al. | 73/49.2 R |
| 3,918,291 | 11/1975 | Pauly et al. | 73/49.2 R |
| 4,078,421 | 3/1978 | Gastaldo et al. | 73/49.2 R |
| 4,350,038 | 9/1982 | Soncrant | 73/49.2 R |
| 4,364,261 | 12/1982 | Askwith et al. | 73/49.2 R |
| 4,776,206 | 10/1988 | Armstrong et al. | 73/40 |
| 4,930,341 | 6/1990 | Euteneuer | 73/37 |

FOREIGN PATENT DOCUMENTS 284403 1/1971 U.S.S.R. ................... 73/37

Primary Examiner—John Chapman
Assistant Examiner—Craig Miller
Attorney, Agent, or Firm—John R. Duncan; Frank D. Gilliam

[57] ABSTRACT

A fluid injection method of nondestructive testing for bonding between two layers of material, at least one of which is penetrable is presented. One or two fluid injection members are inserted at selected locations along the penetrable material to the bond line between the materials. In the single injection member test, a fluid under known pressure is injected through the injection member to the bond line. The flow is measured at several locations and an average flow rate under satisfactory bonding conditions is noted. Any flow rates in excess of some fixed amount above this established norm is considered unsatisfactory. In the two injection member test. The two members are adjacently inserted through the material to the bond line and a fluid under known pressure is injected from one injection member to the bond line. If a disbond exists between the two members, the second member receives fluid from the first at the bond line. If any amount of fluid is received by the second member, a non-bond condition is indicated. Various pressures are chosen depending on injection member size, material thickness, type of penetrable material, etc.

10 Claims, 1 Drawing Sheet

NONDESTRUCTIVE TESTING OF PENETRABLE MATERIAL BOND INTERFACES

BACKGROUND OF THE INVENTION

The invention is directed to the testing for bond line adhesion between two materials and more particularly, non-destructive testing of bonding or adherence between penetrable and non-penetrable/penetrable materials such as, for example, insulation foam on a stainless steel tank surface.

Many adhesive bond lines between penetrable and non-penetrable /penetrable materials presently cannot be inspected with standard non-destructive testing methods. Ultrasonics often cannot be used because ultrasonic energy is usually not transmitted through most penetrable materials. These materials usually are not inspectable by eddy current methods. X-ray inspection requires that there be a density variation, which is usually not present in disbond areas of these materials.

The non-destructive testing method of the present invention fills the long desired need for accurate inspection of adhesive bondlines between penetrable and non-penetrable materials.

SUMMARY OF THE INVENTION

The invention is directed to non-destructive inspecting or testing of bond line adherence between penetrable and non-penetrable materials such as, by way of example, between foam insulation material adhered to the surface of a stainless tank designed for holding cryogenic liquids.

The method of the invention comprises two embodiments. In one embodiment a source of pressurized fluid, generally a gas such as nitrogen gas, by way of example, or any other convenient gas, the output of which is pressure regulated and passed through a flow meter and injected through a needle such as, a hypodermic needle, into the bond line to be tested or inspected. The flow of gas through the flow meter is recorded. A similar test is preformed at several different bond line locations and recorded. A normal expected flow rate is determined from these tests and is used to determine acceptable or non-acceptable (voids) bonding at representative different bonding locations about the material.

In the two needle method a pair of needles such as, hypodermic needles, are employed, a first flow meter as used in the above described method is employed and a second more sensitive flow meter is attached to the downstream end of the second needle. The two needles are inserted to the bond line of the material in a closely adjacent relationship. If there is a continuous disbond or void between the two needles, fluid is passed through the first needle into the bond line. The tip of the second needle receives fluid at the bond line from the output of the first needle through the bond line. The flow rates of the two flow meters are recorded at each test location. Under acceptable bonding, in the first embodiment, the fluid flow will be minimal due to the bonding not allowing the fluid to escape as readily from the tip of the needle as when the materials are not properly bonded wherein the fluid escapes between the materials indicating excess gas flow. In the two needle embodiment, a poor bond along the bond line causes the fluid from the first needle to escape between the two materials resulting in a pressure drop at the tip of the first needle and in a flow at the second flow meter.

An object of this invention is to provide a method for non-destructive testing of bonding between penetrable and non-penetrable penetrable materials.

Another object of the invention is to provide a method of using fluid under pressure released adjacent to the bond line between penetrable and non-penetrable/penetrable materials for determining satisfactory bond lines therebetween.

Another object of this invention is to provide a method of determining satisfactory bond lines between penetrable and non-penetrable materials by monitoring gas flow through the bond line where excessive flow indicates bond line bonding failure.

These and other objects of the invention will become better understood by reference to the following description when considered with the drawing Figures, in which:

BRIEF DESCRIPTION OF THE DRAWING FIGURES

DETAILED DESCRIPTION OF THE PREFERRED EMBODIMENTS OF THE NON-DESTRUCTIVE TESTING OF THE BONDING BETWEEN PENETRABLE AND NON-PENETRABLE/PENETRABLE MATERIALS

Figure 1:
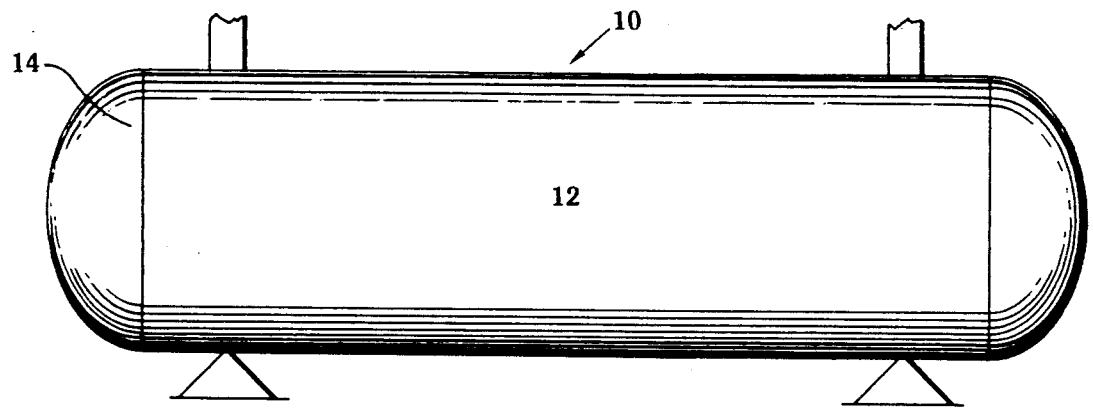
FIG. 1 depicts a stainless steel cryogenic liquid holding tank covered with an insulation material bonded thereto and marked for bond line testing.

Referring now to the various drawing Figures, FIG. 1 depicts a typical use for the two embodiments of the bond line testing of the present invention. An insulated tank 10 constructed of metal such as, for example, stainless steel and having bonded thereto is a layer of foam insulation or other type insulation material 12 bonded thereto designed to contain a cryogenic liquid such as liquid nitrogen or the like. The outer surface of the stainless steel tank is completely covered with the insulation material 12 which is expected to be substantially bonded to the entire outer surface of the tank. It is important that the bonding between the two materials has no voids as any voids may cause a reduction in the mechanical strength and reliability of the system. This could cause a loss of foam and therefore a loss of insulation. The tank may be marked off in a square grid pattern for bond line bond testing with test locations established at intersections thereof. It has been found that a pattern of six inch squares with a flow test performed at each intersection 14 is generally satisfactory.

Figure 2:
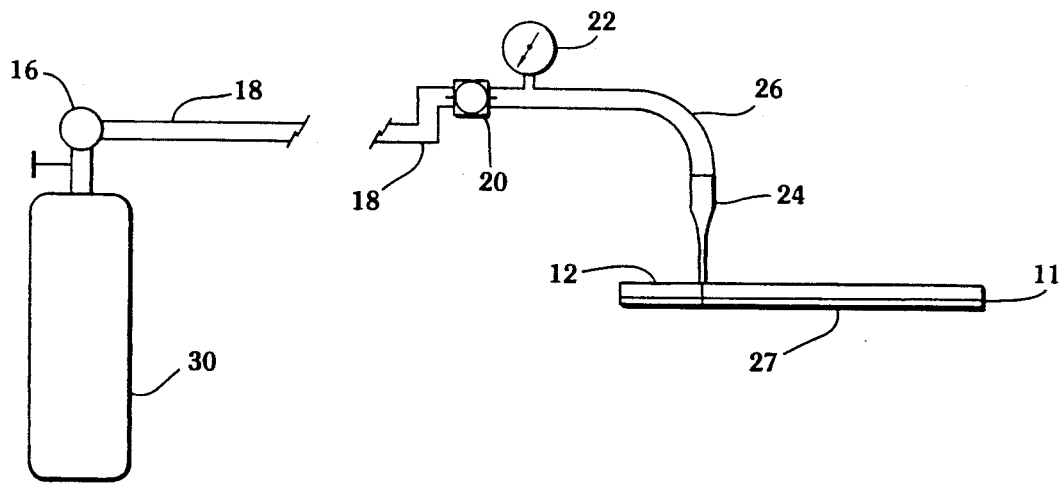
FIG. 2 depicts the first embodiment of the invention for testing bonding of penetrable material bonded to non-penetrable penetrable material.

Referring now to the drawing FIG. 2 which depicts the first embodiment of the invention. This embodiment comprises a source of pressurized fluid (gas) 30, shown as a pressurized tank containing for example nitrogen gas, with a pressure regulator 16 for regulation of the fluid pressure leaving the source 30; A length of pressure hose or line 18 of a required length; A first flow meter 20 having a flow rate for example of 0 to 10 Cubic feet per hour (CFH); a pressure indicator 22 for monitoring the regulated pressure from the source, generally the regulator 16 is set to read 10 PSI on the indicator 22; and A needle 24, hypodermic, syringe or the like such as, for example, a "Yale 20" hypodermic needle or equivalent attached to the distal end 26 of the hose 18.

In operation, the regulator is set to provide a predetermined fluid pressure in the hose with the needle opening closed. The fluid pressure set by the regulator 16 for entry into the hose can be selected at any desired pressure value depending on the test to be performed and the specific equipment used. The needle 24 is inserted into the insulation 12 until it reaches the bond line 11 adjacent to the outer skin 27 of the tank 10. The rate of fluid flow through the flow meter at a given hose or line pressure determines whether or not a satisfactory bond exists at each test location. After several intersection locations are tested for flow rate through flow meter 20, a norm or a satisfactory bond flow rate is established. The remainder of the test intersections are then tested and a flow reading is taken at each intersection. If the flow meter reading at the other intersections is substantially the same as the norm reading, then the bonding at the bond line 11 is considered to be satisfactory. If the flow at any test location is excessive from the normal flow then the bonding of the bonding line 11 at that location is considered unsatisfactory. On a normal satisfactory bond line the only fluid that flows is out the aperture formed by the insertion of the needle through the insulation and penetration flow through the area immediately adjoining the needle tip. On an unsatisfactory bond line, the fluid will in addition to flowing out the aperture, flow along the unbonded bond line and the flow meter will show an excessive fluid due to permeation through the disbounded area flow which is indicative of a unsatisfactory bond line at the test point.

Figure 3:
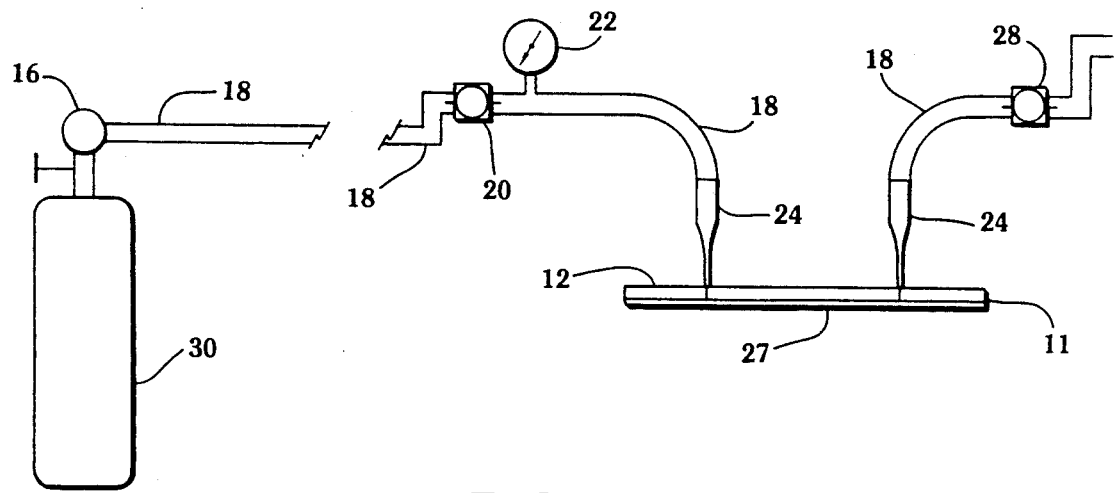
FIG. 3 depicts the second embodiment of the invention for testing the bond line of penetrable material bonded to non-penetrable/penetrable material.

Referring now to the drawing FIG. 3 which depicts the second embodiment of the invention. The second embodiment includes the apparatus of the first embodiment and further includes a second needle 24, hose or line 18 and a second flow meter 28 which more accurately measures a smaller fluid flow than the flow meter 20 discussed above. A flow meter 28 having a flow range of from 0.0 to 0.5 CFH has worked satisfactory for this embodiment. In addition to the first embodiment test sequence in the second embodiment the second needle is inserted adjacent to the first needle. If there is a continuous disbond between the two needles the fluid exiting the first needle is forced into the second needle and the flow therethrough is monitored. The flow meter 28 is monitored and will show an indication when there is a flow into the second needle.

While certain preferred dimensions, materials, configurations and arrangements were detailed in the above description of preferred embodiments, those can be varied, where suitable, with similar results. Other applications, variations and ramifications of this invention will occur to those skilled in the art upon reading this disclosure. Those are intended to be included within the scope of this invention as defined in the appended claims.

What is claimed is:

1. An apparatus for testing for disbounds at a bond line disbond between a metal surface and a layer of insulation material bonded thereto comprising:
   A source of fluid under pressure;
   A pressure regulator for regulating the level of pressure from said source of fluid under pressure exiting said pressure regulator;
   a hollow needle with a opening at each end, a first end of said needle communicating with the fluid under pressure exiting said pressure regulator and the other end for inserting through said insulation material to said bond line adjacent said metal surface; and
   a first flow meter in series between said exit of said pressure regulator and the first end of said needle whereby in the absence of said disbonds a low flow rate will be observed on said flow meter and when a disbond is present a higher then said low flow rate will be indicated by said flow meter.

2. The invention as defined in claim 1 additionally comprising:
   a second hollow needle and
   a second flow meter communicating with a first end of said second needle.

3. The invention as defined in claim 1 wherein a hose is used to communicate said first end of said needle and said first flow meter, and said flow meter and said exit of said pressure regulator.

4. The invention as defined in claim 2 wherein a hose is used to communicate between said second needle and said second flow meter.

5. The invention as defined in claim 1 wherein said first flow meter has a range of from 0 to 10 CFH.

6. The invention as defined in claim 2 wherein said flow meter has a range of from 0 to 0.5 CFH.

7. The invention as defined in claim 1 wherein said first needle is a hypodermic needle.

8. The invention as defined in claim 2 wherein said second needle is a hypodermic needle.

9. A method of non-destructive testing for voids in the bond line between a nonpermeable metal surface and a permeable insulation material bonded thereto comprising the following steps:
   providing a liquid under regulated pressure to one end of a first hollow needle;
   inserting said needle through said insulation material to said bond line adjacent said metal surface; and
   monitoring the flow of said liquid exiting the other end of said hollow needle whereby a small normal flow is expected where no void exists and a larger than a normal flow where a void exists.

10. The method of claim 9 additionally comprising the steps of:
    inserting a second hollow needle adjacent to said first needle through said insulation material adjacent to said first hollow needle and
    monitoring the flow of fluid through said second needle whereby a small flow indicates a disbond.

* * * * *